US011142474B2

(12) United States Patent
Sallustro (10) Patent No.: US 11,142,474 B2
(45) Date of Patent: Oct. 12, 2021

(54) FACILITY AND METHOD FOR BIOLOGICALLY TREATING ORGANIC WASTE AND EFFLUENTS

(71) Applicant: JUA GROUP, Moka (MU)

(72) Inventor: Jean-Luc Sallustro, Trou-aux-Biches (MU)

(73) Assignee: JUA GROUP, Moka (MU)

(*) Notice: Subject to any disclaimer, the term of this patent is extended or adjusted under 35 U.S.C. 154(b) by 465 days.

(21) Appl. No.: 16/062,099

(22) PCT Filed: Dec. 21, 2016

(86) PCT No.: PCT/FR2016/053592
§ 371 (c)(1),
(2) Date: Jun. 13, 2018

(87) PCT Pub. No.: WO2017/109398
PCT Pub. Date: Jun. 29, 2017

(65) Prior Publication Data
US 2018/0370829 A1     Dec. 27, 2018

(30) Foreign Application Priority Data

Dec. 21, 2015 (FR) ........................... 1562898

(51) Int. Cl.
*C02F 3/28*     (2006.01)
*C02F 3/00*     (2006.01)
(Continued)

(52) U.S. Cl.
CPC .............. *C02F 3/2893* (2013.01); *C02F 3/00* (2013.01); *C02F 3/286* (2013.01); *C02F 3/2873* (2013.01);
(Continued)

(58) Field of Classification Search
CPC ...... C12M 21/04; C12M 27/02; C12M 23/34; C12M 29/14; C12M 29/24; C02F 3/28;
(Continued)

(56) References Cited

U.S. PATENT DOCUMENTS

| 4,780,415 A | 10/1988 | Ducellier |
| 5,560,819 A | 10/1996 | Taguchi |

(Continued)

FOREIGN PATENT DOCUMENTS

WO     2011017420 A2     2/2011

*Primary Examiner* — Claire A Norris
(74) *Attorney, Agent, or Firm* — Jordan IP Law, LLC; Todd A. Vaughn (57) ABSTRACT

The facility comprises: —a first tank (1) comprising separation means (15) extending over a portion of the height of the tank, so as to define a central compartment, or tube (11), a peripheral compartment, or ring (12), and a compartment for stirring and biochemical exchanges (16) in the bottom portion of the tank, comprising stirring means (17), —a second tank (2) comprising separation means (25) extending over a portion of the height of the tank, so as to define a central compartment, or tube (21), a peripheral compartment, or ring (22), and a compartment for stirring and biochemical exchanges (26) in the bottom portion of the tank, comprising stirring means (27), —means (ALIM) for feeding the waste to be treated into the first ring—means (T) for transferring the partially treated waste from the first tube to the second ring, —means (EVAC) for discharging the treated waste out of the second tube, —advantageously pneumatic means (4, 43, 44) for circulating the waste from the first ring to the second tube.

17 Claims, 3 Drawing Sheets

(51) Int. Cl.
*C02F 11/04* (2006.01)
*C12M 1/107* (2006.01)
*C12M 1/00* (2006.01)

(52) U.S. Cl.
CPC ............ *C12M 21/04* (2013.01); *C12M 23/34* (2013.01); *C12M 23/58* (2013.01); *C12M 29/14* (2013.01); *C12M 29/24* (2013.01); *C02F 11/04* (2013.01); *C02F 2203/006* (2013.01); *Y02E 50/30* (2013.01)

(58) Field of Classification Search
CPC ........ C02F 3/286; C02F 3/2873; C02F 11/04; C02F 3/2893
USPC .................................. 210/603, 218
See application file for complete search history.

(56) References Cited

U.S. PATENT DOCUMENTS 6,328,892 B1 * 12/2001 Jones ............... C02F 3/226
210/605
2012/0156744 A1 * 6/2012 Macdonald ........... C12M 23/58
435/155

* cited by examiner

FACILITY AND METHOD FOR BIOLOGICALLY TREATING ORGANIC WASTE AND EFFLUENTS

CROSS-REFERENCE TO RELATED APPLICATIONS

The present application is a National Stage Application of PCT International Application No. PCT/FR2016/053592 (filed on Dec. 21, 2016), under 35 U.S.C. § 371, which claims priority to French Patent Application No. 1562898 (filed on Dec. 21, 2015), which are each hereby incorporated by reference in their respective entireties.

TECHNICAL FIELD OF THE INVENTION

This invention relates to a facility for treating organic waste and effluents via biodigestion, as well as a method for implementing this facility. The invention relates to the optimisation of biomethanisation protocols of organic substrates, waste and effluents in a multiphase digester with semi-continuous feed of the piston type, accepting a high content in volatile organic materials under thermophilic conditions. The invention relates in particular to the geometry of the different elements that comprise this facility, as well as to the dynamics of the exchanges between these constituting elements.

PRIOR ART

The treatment of organic materials via biodigestion is above all subjected to biological constraints that the techniques try to respect that aim to create and maintain an ecosystem that is favourable for micro-organisms that are particular to this type of bio-oxidation. By simplifying it is possible to say that a biodigester that it receives and maintains in a system of bioreactors populations of strictly anaerobic microbes which are led to grow and to reproduce on an organic substrate comprised of waste or more generally liquid or solid materials placed into solution. For the most part these particular microbial populations develop a bio-oxidation activity, but in the absence of oxygen in the air. The reaction is possible only when the three bacterial communities that are typical of this trophism form a balanced ecosystem in such a way that most of the reducing equivalents (atoms of carbon and of hydrogen) produced as waste during the bacterial anabolism (hydrolysis then *acidophilus* and acetogenesis) are finally found in the methane ($CH_4$, methanogenesis). The bacterial species concerned are complex and relatively varied but their biochemical characteristics and the major lines of their ecology are known rather well. They are generally classified into three groups:

The hydrolytic and fermentative bacteria.
The acetogenic bacteria.
The methanogenic bacteria.

The management of the artificial ecosystem that an anaerobic bioreactor forms therefore requires a dynamic intervention in order to ensure certain physical-chemical conditions, such as the pH, the temperature and the redox potential, as well as the nutritional needs.

The pH: The optimum pH for anaerobic digestion is situated around neutrality. It the result of the optimum pH of each bacterial population: that of acid-forming bacteria is between 5.5 and 6, acetogenic bacteria prefer a pH close to neutrality while methanogenic bacteria have a maximum activity in a pH range between 6 and 8. However, the methanisation can occur in slightly acidic or alkaline mediums.

The temperature: The activity of the methanogenic consortium is closely linked to the temperature. Two optimum temperature ranges can be defined: the mesophilic zone (around 35° C.) and the thermophilic zone (between 55-60° C.) with a decay in the activity on either side of these temperatures. Most of the bacterial species have been isolated in mesophilic environments, but all of the trophic groups of the steps of anaerobic digestion have thermophilic species that use the same metabolic channels as the mesophilic bacteria with similar or superior performance. It however remains possible to work at temperatures that are different from optimum temperatures with lower or higher performance levels.

The redox potential: This parameter represents reduction state of the system, it affects the activity of the methanogenic bacteria. These bacteria in effect require, in addition to the absence of oxygen, a redox potential less than 330 mV in order to initiate their growth.

The nutritional and metabolic needs: As with any microorganism, each bacterium comprising the methanogenic flora requires a sufficient supply of macro-elements (C, N, P, S) and of trace elements for its growth. The needs in macro-elements can be assessed roughly from the raw formula describing the composition of a cell ($C_5H_9O_3N$). For methanogenic bacteria, the culture medium must have contents in carbon (expressed as Chemical Oxygen Demand or COD), in nitrogen and in phosphorus at least in the proportions COD/N/P equal to 400/7/1.

Ammonia is their main source of nitrogen. Certain species fix the molecular nitrogen while others need amino acids. The needs in nitrogen representing 11% of the volatile dry mass of the biomass and the needs in phosphorus ⅕ of those of nitrogen.

The methanogenic bacteria have high contents in Fe—S protein which play the major role in the electron transporter system and in the synthesis of coenzymes. Also the optimum concentration of sulphur varies from 1 to 2 mM (mmol/L) in the cell. This flora generally uses the reduced forms such as hydrogen sulphide. The methanogenic bacteria assimilate the phosphorus in mineral form.

Certain trace elements are required for the growth of the methanogenic bacteria. This is more particularly nickel, iron and cobalt. Indeed, these are constituents of coenzymes and of proteins involved in their metabolism. Magnesium is essential since it comes into play in the terminal synthesis reaction of the methane as well as the sodium appearing in the chemical-osmotic process in the synthesis of Adenosine Triphosphate (ATP).

There are growth factors that stimulate the activity of certain methanogenic bacteria: fatty acids, vitamins as well as complex mixtures such as yeast extract or the trypticase peptone. In conclusion, although the macro-model" which simulates a biodigestion process is correctly controlled today, to the point that it is possible to summarily predict the extent and the form of the methane productions and the composition of a digestate or methacompost, it still remains nevertheless that the methods are difficult to implement. Indeed, if it is desired to treat a given organic effluent, the fermentable fraction of the household and similar waste or some industrial organic waste or coming from agricultural sectors, or a mixture of inputs (co-digestion) the process for reaching the best productivity must each time be dedicated. Indeed, to each substrate corresponds an optimum microbiological ecosystem and the slots for biochemical output are narrow. In other terms, the challenge consists in designing and in implementing a methane digester with low investment and low operating costs but which is perfectly versatile, in order to provide a high methane productivity regardless of the variation of the constraints of the inputs.

However the recent empirical and analytical approach of which biodigestion benefits, rather than versatility, has made it possible to generate a certain number of functional laws which are applied to biodigestion technologies that are varied but not variables, with each one having a privileged adaptation to the treatment of a certain type of waste, in variable quantities with different qualities of methacompost and biogas.

The Different Methods

A bioreactor under anaerobic conditions is an artefact that attempts to optimise the living conditions of a given colony of micro-organisms at a given moment and/or in a given place so as to concentrate in a minimum of biological retention time, therefore in a minimum bioreactor volume, the maximum production of methane that results from the digestion of the substrates placed in an aqueous solution or more generally in the absence of gaseous oxygen. By simplifying, we can say that a biodigester is formed of four major components:

An enclosure that is sealed and often thermally insulated
An agitation or stirring device
A device for heating digestates
Inlet and outlet devices for the substrate, the digestate and the biogas.

According to the methods implemented two major types of ecosystems can be distinguished:

Fixed biomass
Free biomass

In a fixed biomass digester, the enclosure is used not only to contain the substrate and insulate it from air, but also to fix anaerobic bacterial colonies on adapted supports. Certain liquid phase techniques use autonomous binding cells which are immersed in the flow. Generally, the advantage of this method resides in maintaining the availability of the bacterial strains despite the permanent or sequential transfer of the flow of substrates treated, with the objective sought being to not have to restart a bacterial seeding or avoiding having to specialise the flora with chemical additives. Several types of binding methods are available, some for example granulate the substrate or a portion of the input substrate before seeding and having it circulate in the enclosure of the biodigester.

As a general rule, the operations of bio-oxidation of the waste or organic materials must meet several criteria of effectiveness and of biosafety that are carried out by performing critical settings and adjustments. As such, in a free or fixed biomass digester, use is made of methods that reinforce the active biomass which result from the heating and from the circulation of the liqueurs and, optionally, additions of trace elements and pH correctors. The method can be adapted and takes up the challenge of the spontaneous capacity of the bacterial flora to become specialised according to the constraints of the medium, in particular concerning the presence of nutrients in a substantial quantity. The adaptability of the biomass, left free to leave the enclosure with the sequential or continuous stream of the flows, and to change according to the stresses of the ecosystem, is reinforced by "external", thermal (maintaining in mesophilic conditions at 36° C. or thermophilic conditions at 55° C.), chemical (neutralisation of the acidic or alkaline pH) and mechanical (transfers, fluidising and stirring) actions. As a general rule a biodigester therefore requires either good following of the indications supplied by the sensors, so as to allow for a human response for adjusting in a deferred time, or the analysis and automatic treatment of the signals transmitted by sensors inferring in real time the actuating of effectors.

Beyond the differentiation between fixed biomass and free population, manual or automatic adjustments, two types of flow dynamics are also distinguished:

Sequential loading.
Continuous supply.

Sequential loading methods have as a major characteristic that they seek to establish, in the same enclosure for a single dose of substrate, the succession of the major phases of the methane digestion. In other words, it can be considered that, in this context, the bacterial populations develop on an identical substrate from the start to the end of the cycle and therefore do not need to expend energy in order to adapt to unexpected changes in their ecosystem, they are what transform it, not the other way around. As such as soon as the loading of the tank is complete, and this can be done in one day as in three or four days, the optimum conditions for starting the hydrolysis phase are provided (temperature, pH, nutrients, seeding). It is then the transient phase of acidogenesis that is adjusted in order to allow for the triggering of the acetogenesis and finally the methanogenesis. In theory this method has the interest of having a Hydraulic Retention Time (HRT) that is shorter than that of the continuous flow protocols and of being easier to control. Generally several tanks must be available operating in parallel which are activated one after the other as they are filled. In the event of a malfunction of a cell, the treatment can continue with the others. This is also a method where the tanks are smaller and which generally accept denser substrates in dry matter. However, sequential loading requires multiplying the enclosures and the related devices such as loading hoppers, valves and other pumps.

Continuous supply is strictly opposite sequential loading on several points. Firstly, because the ecosystem and particularly the bacterial flora are brought to be versatile, or rather to coexist in the same enclosure and at the same time, but not necessarily in the same layer or stage of the bioreaction volume, bacteria and their co-enzymes for the four phases of the cycle. Then because, in order to obtain a sufficient HRT, the tank has to be dimensioned over very substantial volumes. This results in proportional energy expenses in order to maintain a suitable temperature (very rarely thermophilic except on small units) and especially for stirring the mixture continuously, in order to prevent the formation of a crust on the surface and excessively dense sediments at the bottom of the tank. It must however be noted that this method, which is very old since Chinese domestic or farm biodigesters are mostly supplied continuously, adapt well to the micro-deposits of homogeneous organic substrates with very low variability. Indeed with very small dimensions (a few tens of m$^3$), quality waste and a stable quantity, they are easy to maintain in so far as it is not sought to discharge the sediments in real time but rather the flows in liquid or turbid phase (called eluates) that can then be recycled for spreading. However after several operating cycles these small units must be stopped and emptied of their sediments which, due to the accumulation, reduce the useful volume of the facility and are detrimental to the development of the bacterial flora. Only certain industrial methods manage to produce in addition to biogas, very loaded flows from which are extracted via decantation and/or wringing of the methacomposts (digestates) which can be recycled as solid biological fertiliser. The advantage of this method, on an industrial or domestic level, therefore resides substantially in its capacity to accept a continuous flow of waste or of effluents with a low organic load with medium productions of biogas but a possible recycling of the extracted effluents and more difficultly of the methacompost.

Based on what has just been described, two major types of methods continue to compete:
  Single phase.
  Differentiated phases.

In the first case, whether the biodigester is of the sequential or continuous type, with a fixed or free biomass, all of the phases take place in the same enclosure. This subsystem is either via gravity (sedimentation) or with counter flow and it has the wide majority. The fundamental technological variations concern the modalities of the sequential or linear mixing of the substrates (stirred, in opposition to pulsed and infinitely mixed), the modalities for introducing substrates and extracting digestates and eluates.

In the second case and in theory, each one of the four phases can be confined in a separate tank and the passage of the substrate modified at the end of each phase towards the next is provided by a mechanical or hydraulic system. In reality the state of the art clearly favours bi-phase systems within which hydrolysis and acidogenesis are confined in a first enclosure while the acetogenesis and the methanogenesis are provided together in the second enclosure. The purpose sought by these multiphase methods is to better manage the phases individually by varying the micro-conditions that optimise these different ecosystems. More complex and expensive, methods with differentiated phases however have better output in terms of biodegradability in particular for substrates that require a high enzymatic speciation and/or a particular chemical or thermal environment. However for a flow of waste that is homogeneous over time and with a composition that does not offer any particular risks (especially at the acetogenesis stage) it is generally considered that this method does not provide any value added that is sufficient to legitimise the complexity and the investment required.

Finally, a distinction is made between three types of biodigesters according to the concentration of Total Suspended Solids (TSS) in the flows, i.e. the proportion of dry matter (DM) suspended in the digester:
  Low concentration in DM with less than 10% in TSS.
  Medium concentration in DM containing between 15% and 20%, in TSS.
  High concentration in DM containing between 22% and 40% TSS.

The applications of the principle of biodigestion of flows with a low content in TSS have as main inputs industrial or domestic effluents, as is the case for example for wastewater treatment plants for urban wastewater. Biodigesters that are applied to treating these flows have a particular configuration, the principle consists in using the biodigester as a sedimentation tank wherein the TSS are retained and treated anaerobically while a flow of purified water escapes therefrom. More clearly said, the Biological Retention Time (BRT) of the TSS is therein more substantial than that of the input flow in terms of Hydraulic Retention Time (HRT) as the biodigester integrates a passive or active decantation system and an anaerobic retention/degradation system for digestible DM.

As such these biodigesters are improper for treating solid organic waste except that the latter is crushed and placed in solution with effluents that will always constitute most of the input. Under these protocols, the production of biogas and of methacompost (here in the form of sludge) is relatively low but their primary purification capacity of an effluent is very good and their energy balance is balanced with the cogeneration of the biogas. Optionally the productivity of these subsystems is improved with the resale of the digestate liqueurs (eluates) as liquid organic fertilisers. The maximum volume loads that can be applied are about from 2 to 5 kg of $COD/m^3/d$.

The type of biodigester with a medium concentration in TSS is the most common, under this configuration a solid digestible substrate is placed in solution in 2 times to 3 times its weight in water. This modality of density in organic matter placed in solution corresponds to the search for a balance between the quantity of digestible material, its viscosity and its coalescence in the enclosure of the digester and the capacity of the anaerobic medium to shelter and maintain degrading bacterial populations without risking inhibiting them via biochemical saturation. Indeed, so that the bacterial activity takes place in the best conditions it is necessary that the digestate does not become compact as long as it can be mobilised as the different phases of biodigestion take place. This method therefore adapts to the treatment of the digestible fraction of the solid organic waste subject to effective sorting upstream in order to discharge the undesirables and a relatively fine crushing that authorises the hydraulic transfer of the digestible mass and the proliferation of a high bacterial diversity. More suitable for methods with continuous rather than sequential loads the principle of the medium concentration in DM particularly benefits fixed biomass systems because the flow of substrate has a flow rate that is substantial enough to deplete the resident flora. Generally, the volume loads to be applied can reach 15 to 20 kg $COD/m^3/d$. The hydraulic residence times vary between 4 and 5 weeks. Under this configuration the outputs in biogas are good and the production of methacompost in the form of settled fibred material is correct but requires for the least a decantation if not a centrifugation.

Certain deposits of organic waste are formed from a substantial solid fraction with low digestibility. Clearly, the mass of DM is substantial but the proportion of Volatile Organic Material (VOM) over the DM is not substantial. In that it is not possible to validly concentrate the VOM of this waste it is appropriate to have a technology that allows for the treatment thereof anaerobically and certain biodigesters are designed for this type of application. They are referred to as High concentration in DM.

The specificity of these applications resides in the method of progression and of stirring of the substrate and in the fact that it is almost exclusively bioreactors with sequential loading and with a free biomass, but with seeding. Generally, it is necessary to note that beyond a certain threshold in VOM content, there is a risk of overloading which can result in an inhibition of the methanogenesis which is especially valid for waste that is rich in animal protein (carcasses and fats). In addition the volume loads to be applied can reach 40 kg $COD/m^3/d$. The hydraulic residence times vary between 2 and 3 weeks.

The fact must as such be taken into account that beyond 3 g/L, ammonia ($NH_4^+$) is an inhibitor of the methanogenesis. It is also known that this limit of 3 g/L of $NH_4^+$ must not be exceeded for waste of which the C/N ratio is less than or equal to 20 with a VOM content of about 60% of the OM.

The mostly commonly practiced technique for maintaining the organic substrates below this threshold consists in mixing the waste that is excessively rich in proteins (viscera, fish, milk products, carcasses and other meat waste) with carbon substrates. The alternative to the approach via regulation of the mixture consists in lowering the VOM content of the waste (especially the proportion of ammonia) by subjecting them to a prior phase of intense thermophilic aerobic fermentation, but the latter requires in any case that the meat waste be mixed with carbon substrates.

Through WO-A-2011/017420 a bioreactor is known formed from two modules placed in series, of which each one comprises compartments placed side by side. The organic matter to be treated is admitted, via an inlet tube, at the lower portion of the first module. It then circulates along compartments of this module, under the presumed effect of a gaseous current injected in the lower portion of each one of these compartments and which is assumed to create a rising convection.

During this travel in the first module, acetate is formed. The substrate is then admitted into the second module, where is follows a similar path along its constituting compartments. Downstream of this second module, methane is created.

This known bi-phase solution however has certain disadvantages. Indeed, the facility described in WO-A-2011/017420 is not satisfactory for the treatment of substrates with a high solid content, but is rather suitable for highly diluted substrates. Indeed, the method of stirring obtained due to the passage from one cell to the other cannot be suitable for highly turbid materials of which the sedimentation would be increased, due to the turbulences created at the bottom of the system and on the edges of the flow in the upper portion. This facility is sensitive to the phenomena of clogging, as soon as the turbidity reaches a critical threshold. Only a liquid fraction carrying with it light fines with a lift that is sufficient to be moved by the gaseous current can fully pass through the facility, while the heaviest portion tends to settle in the lower portion, which creates blocking zones which rapidly oppose the good flow of the gaseous current. This facility requires the setting up of a powerful and fast gaseous current, which tends to generate high turbulence and, consequently, is detrimental to the setting up of suitable biochemical reactions. In addition such a current with a high velocity does not allow for sufficient biological retention time (BRT).

OBJECTS OF THE INVENTION

In light of the above, the invention aims to overcome the disadvantages of prior art mentioned hereinabove. It aims in particular to propose a facility of which the compactness is improved, which is more robust in particular as it is comprised of a reduced number of constituting elements, and of which the output is improved. The invention also aims to propose such a facility, which radically favours versatility and modularity of the technical means raised in order to offer an investment/productivity ratio that is much more favourable than the average offer on the market.

To this effect, the invention has for object a facility for treating organic waste, in particular with a low or high content in weakly polymerised volatile solids, in order to produce biogas and recover at least one portion of the biogas produced, said facility comprising:
  a first tank comprising first separation means extending over a portion of the height of the tank, so as to define a first central compartment, or tube, a first peripheral compartment, or ring, as well as a first compartment for stirring and biochemical exchanges providing the communication between these two compartments, in the bottom portion of the tank, the first compartment for stirring comprising first stirring means,
  a second tank comprising second separation means extending over a portion of the height of the tank, so as to define a second central compartment, or tube, a second peripheral compartment, or ring, as well as a second compartment for stirring and biochemical exchanges providing the communication between these two compartments, in the bottom portion of the tank, the second compartment for stirring comprising second stirring means,
  inlet means for the waste to be treated, into the first ring, advantageously with a balanced distribution over the four faces of this first ring if it is of square or rectangular section, at the four quadrants of a disc if the tank is cylindrical,
  means for transferring the partially treated waste, from the first tube to the second ring, advantageously with the same balanced distribution on the four faces of the second ring if it is of square or rectangular section, at the four quadrants of a disc if the tank is cylindrical,
  means for discharging treated waste, out of the second tube,
  means for circulating the waste, from the first ring to the second tube.

According to other features of this facility, taken separately or according to any technically permissible combination:
  the means for circulating the waste comprise pneumatic means for circulating the waste,
  the means for circulating the waste comprise non-destructive means of pumping,
  the means for transferring the partially treated waste define a zone for biochemical exchange and transition,
  the pneumatic means for circulating comprise means for pressurising a gas, advantageously an anaerobic gas such as a biogas, nitrogen or carbon dioxide, in particular a pressure tank, as well as at least one duct intended to convey this gas from the means for pressurising to the first ring and/or the second ring,
  the pneumatic means comprise first pneumatic means emptying into the first ring, as well as second pneumatic means emptying into the second ring,
  the stirring means comprise at least one duct intended to convey a stirring gas, advantageously an anaerobic gas such as a biogas, nitrogen or carbon dioxide, with this duct supplying nozzles provided on the side wall of a respective ring,
  the means for transferring the partially treated waste comprise a transfer line connecting an outlet of the first tank and an inlet of the second tank, said outlet being at an altitude that is higher than that of said inlet,
  the facility further comprises means for floating sediments, provided in the vicinity of the bottom of at least one tube,
  the means for floating sediments comprise at least one duct intended to convey a micro-bubbling gas, advantageously an anaerobic gas such as a biogas, nitrogen or carbon dioxide, with this duct supplying at least one micro-bubbling device provided in the vicinity of the bottom of a respective tube,
  in its thermophilic or mesophilic configuration, the facility comprises means for heating tanks,
  the means for heating comprise at least one network of radiant pipes arranged on the inner walls of the rings and/or on the bottom of these rings and/or on the bottom of the tubes, the facility comprises a single first tank comprising a single central compartment and a single peripheral compartment, as well as a single second tank comprising a single central compartment and a single peripheral compartment, for each tank, the central compartment and the peripheral compartment communicate only at the bottom of the tank, by the intermediary of said compartment for stirring and biochemical exchanges.

The invention also has for object a method for implementing a facility for treating organic waste such as defined hereinabove, said method comprising the following steps:

waste to be treated is admitted into the first tank at least one portion of a step of hydrolysis is carried out in the first ring and at least one portion of a step of acidogenesis in the first tube, the partially treated waste is transferred from the first tube to the second ring, at least one portion of a step of acetogenesis is carried out in the second ring and at least one portion of a step of methanogenesis in the second tube, the treated waste is discharged, out of the second tube.

According to other features of this method, taken separately or according to any technically permissible combination:

the means for circulating are activated, in such a way as to circulate the waste, from the first ring to the second tube.

a gaseous fraction rich in biogas is extracted from the treated waste and at least one portion of this extracted gaseous fraction is sent back into at least one tank, a gaseous fraction rich in carbon dioxide is extracted from the treated waste and at least one portion of this gaseous fraction rich in carbon dioxide is sent back into at least one tank, a fraction of the waste present in the second tank is discharged, then another fraction of waste is admitted into the first tank, with the discharged fraction and the admitted fraction having substantially the same volumes, the heating circuit is activated which forms a closed and perfectly sealed loop, by heating the heat transfer fluid that it contains via any suitable means, of a type known per se, preferably by recycling the heat dissipated by an electric generator consuming all or a portion of the biomethane produced by the facility, for each tank, different receiving capacities and therefore different biological retention times are assigned to the central compartment and to the peripheral compartment, the substrates are transferred only by pneumatic forcing, from the first peripheral compartment in succession to the first central compartment, then to the second peripheral compartment and to the second central compartment, and finally out of the second central compartment.

This invention relates to a facility and a method for anaerobic multi-phase digestion with continuous feed of the piston type, with a high content in volatile organic solids, with fixed or free biomass and preferably thermophilic. On the one hand, the facility in accordance with the invention results from a specific architectural design and, on the other hand, the method in accordance with the invention emphasises a particular mode for transferring substrates and fluids within the bioreactor.

The application of a particular architectural design has made possible the differentiation of four cells within a single bioreactor, with each cell being a volume wherein mostly one of the four main phases of the anaerobic biodigestion takes place. The four cells are firstly in interaction two-by-two due to the fact that the first shelters the second which is concentric, in the same way as the third shelters the fourth which is similarly concentric. In addition each pair of concentric cells comprises at its bottom point a common volume of transition and horizontal bioturbation at the sediment stage.

The radiant heating circuit is advantageously adjusted, according to the configuration, to transport a heat transfer fluid brought and maintained according to the thermophilic or mesophilic configurations.

Finally, the second pair of cells advantageously comprises a bioturbation zone from the top point to the low point with sediment dynamics. The bioturbation zones are particularly rich in biochemical and bacterial exchanges.

According to an advantageous feature of the invention, the pneumatic stirring, micro-bubbling and circulation system of the substrate does not destructure the microbiological biomes that form specifically within each phase volume but retained them in a configuration of spontaneous granulation. This provides the method with remarkable effectiveness in accordance with the invention.

The facility and the method of treatment, in accordance with the invention, clearly stand out from the teaching of WO 2011/017420. The system described in this document is a bi-phase system, while the facility and the method of the invention has four, physically separated and sequentially united in a piston system. Here there is a first ring that communicates at the bottom of the tank with a first tube, which communicates via a top pipe exclusively with the top of the second ring, which communicate exclusively at the bottom of the tank with the second tube 2, which communicates exclusively at the top of the tank via a pipe with the device for wringing digestates.

In the method of WO 2011/017420, due to a constant stirring and an interior architecture comprising open tubes, it is not really possible to determine if the first tank is more suitable for favouring hydrolysis or acidogenesis, with the interior compartments being open on the top and the bottom, the volume of this biotank is not exclusive at one or the other of these phases. The same applies in the second tank where the decomposition of acetate and methanogenesis are indissociable. In this method the phase separation is manifestly physical-chemical rather than biochemical in that the stirring by bubbling and the interior architecture of the tanks seems made to separate the floating materials from the settled materials, rather than for reserving a separate and sequential biological residence time for the substrates in the volumes separated during the four biochemical phases of protocol of anaerobic digestion.

In summary, the method according to WO 2011/017420 A2 is organised around a tubular architecture that structures two separate biotanks, inside of each one are installed three tubes open at their two ends, therefore without separation of the substrates inside each biotank. The invention structures each one of its 2 biotanks into two volumes, the ring and the tube, which communicate only at the bottom of the biotank in a bioturbation zone that provides for the phase transition. The invention therefore organises strictly four volumes with each having a different receiving capacity and therefore different biological retention times. In the method of the invention, the transfer of the substrates from the first volume 1 in succession to the second, third and fourth volumes, then from the fourth volume to the outlet of the digester is possible only thanks to the pneumatic forcing carried out according to the invention.

The method of WO 2011/017420 A2 carries out a constant gaseous stirring that assimilates its operation to that implemented in the digesters with infinitely mixed content. As such each one of the two biotanks of WO 2011/017420 A2 is subjected to a permanent convective movement of the substrates, with transfer via overflow from one tube to the other inside the same tank. In this method it is the adding of a dose of substrate at the inlet of the first tank that determines the gravity flow via siphon from the first tank to the second.

In an entirely different manner, the method of the invention uses the stirring gases to create a sufficient pressure in the gas blanket of the closed ring in its upper portion, in order to cause to rise via reaction in the tube open at its upper portion a given quantity of substrate that corresponds to the volume of the dose of the primary substrate coming into the system. This overpressure is obtained when the gas circuit circulated in the biotanks is closed and when the pipe which connects the top of the first tube to the surface (top) of the second ring is open. Identically, when it entails proceeding with discharging digestates the pressure accumulated on the gas blanket of the second ring exerts a thrust on the volume of substrate contained in this ring which, by reaction, rises in the second tube of which the has been opened in its upper portion which reaches the device for wringing digestates. Contrary to the method WO 2011/017420 A2, according to the invention the volume corresponding to that of the incoming materials must be discharged from the second tube, before introducing the incoming substrates into the first ring. In summary the method of WO 2011/017420 A2 is an infinitely mixed digester with two phases with separation of floating materials and a continuous gravity feed, while the method of the invention is piston digester with four phases with semi-continuous feeds with forcing.

The method of WO 2011/017420 A2 uses a froth separator associated with gas pumps of the tesla type that mobilise the bubbling gases said device is also supposed to produce a partial discharge of the materials floating in the tanks. The method of the invention introduces, on the contrary, anaerobic gas separately in the bottom portion of the ring or of the tube of each biotank in such a way as to create a micro-bubbling at low pressure. The latter will generate the bioturbation conditions sought in this bottom zone in order to install and maintain the local mixing parameters with micro perturbation which allow for the biochemical phase transition. In the method according to the invention, the bubbling of the mixer effects is carried out all along the riser column. It is also possible to carry out a stirring by pulses or spasms by creating pressure conditions in the gas blankets of the rings that do not reach the full transfer point that would lead the substrate to overflow from the tube, and by releasing this pressure quickly in order to create a vertical reflux effect that very significantly favours the stirring and the mixing of the floating elements via abrupt aspiration in the down column.

Due to its configuration, the method of WO 2011/017420 A2 is specially designed for liquid or diluted substrates while the method of the invention lends itself equally perfectly and particularly to substrates with a medium and high content in total solids and even at high viscosity. The management of the temperatures announced for this prior method is therefore 75° C. in tank 1 and 55° C. in tank 2. The method of the invention favours, on the contrary, advantageously a particular bacterial population (*pseudomonas*) in the ring 1 which is maintained typically at 40° C. while the tube 1 which is concentric is maintained typically at 35° C., likewise the ring 2 is maintained typically between 50° C. and 52° C. when the tube 2 is brought typically to 55° C. This temperature regulation is automated in the method of the invention and is made possible by heat transfers at the bottom of the tank carried out with separated radiant immersed tubes. In addition, particularly in the tubes, the fine management of the temperature and of the flows of stirring gases allows for the thermal discrimination sought.

DESCRIPTION OF THE FIGURES

FIGS. 1 to 4 show embodiments of the invention, but do not limit the scope of the invention.

The following numerical references are used in this description:

| 1 | First tank | 2 | Second tank |
|---|---|---|---|
| 11 | Tube | 21 | Tube |
| 12 | Ring | 22 | Ring |
| 13 | Bottom | 23 | Bottom |
| 14 | Lid periphery | 24 | Lid periphery |
| 14' | Lid centre | 24' | Lid centre |
| 15 | Separation wall | 25 | Separation wall |
| 15' | Indentations | 25' | Indentations |
| 16 | Common zone | 26 | Common zone |
| 17 | Stirring device | 27 | Stirring device |
| 17' | Micro-bubbling device | 27' | Micro-bubbling device |
| 19 | Outer jacket | 29 | Outer jacket |
| E1 | Substrate inlet | T | Transfer line |
| ALIM | Supply line | E2 | Supply line |
| S1 | Substrate outlet | S2 | Substrate outlet |
| EVAC | Substrate discharge | 31, 31' | Biogas outlet |
| 43, 44 | Circulation gas inlet | 47, 48 | Stirring gas outlet |
| 3 | Wringer screw | 32 | Digestate outlet |
| 33 | Eluate outlet | 4 | Pressure tank |
| 41, 42 | Outlets of 4 | 45, 46 | Lines from 4 to 2 |
| 5 | Filtration device | 51 | Outlet of 5 |
| 52, 53 | Lines from 5 to 1 | BIO | Bioturbation zone |

DETAILED DESCRIPTION

Figure 1:
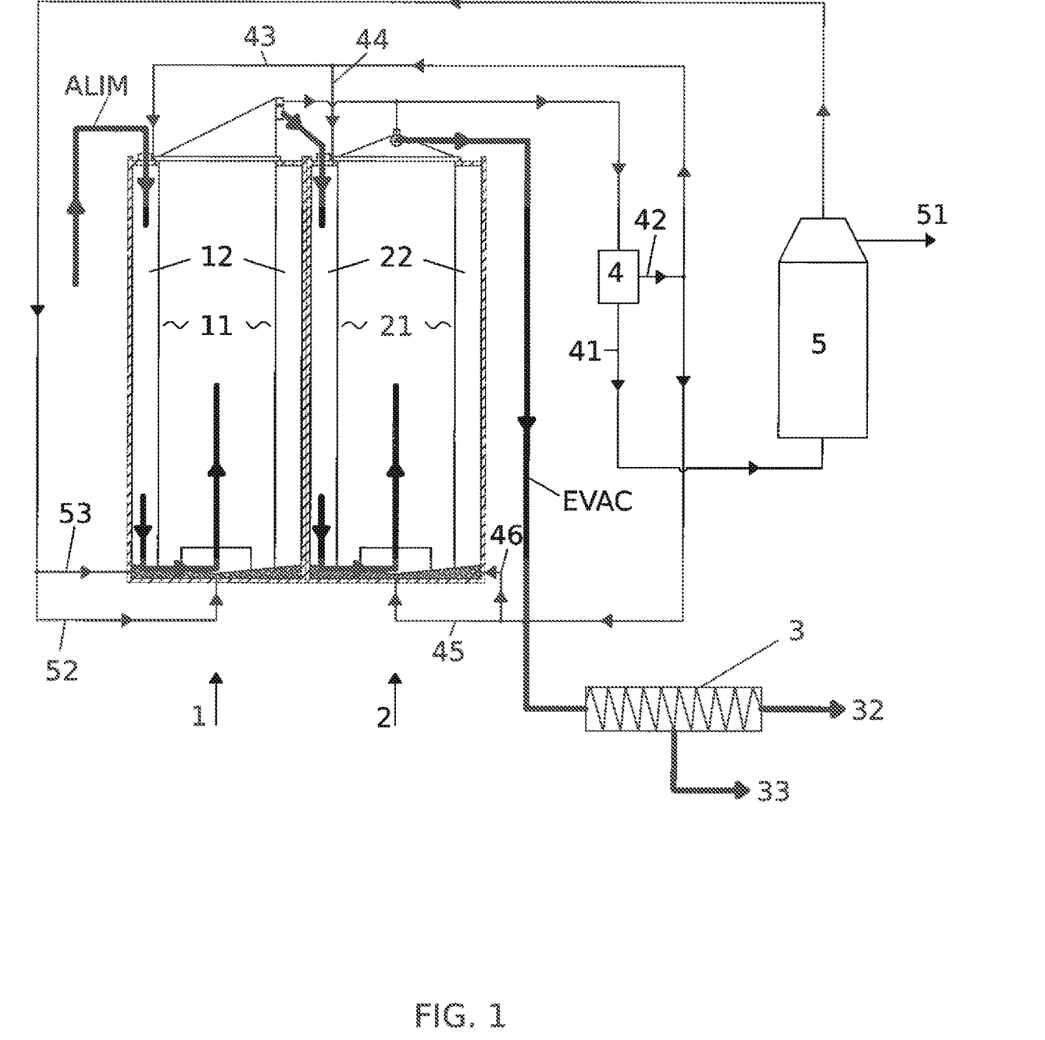
FIG. 1 is a diagrammatical view, showing a waste treatment facility in accordance with the invention.
Figure 2:
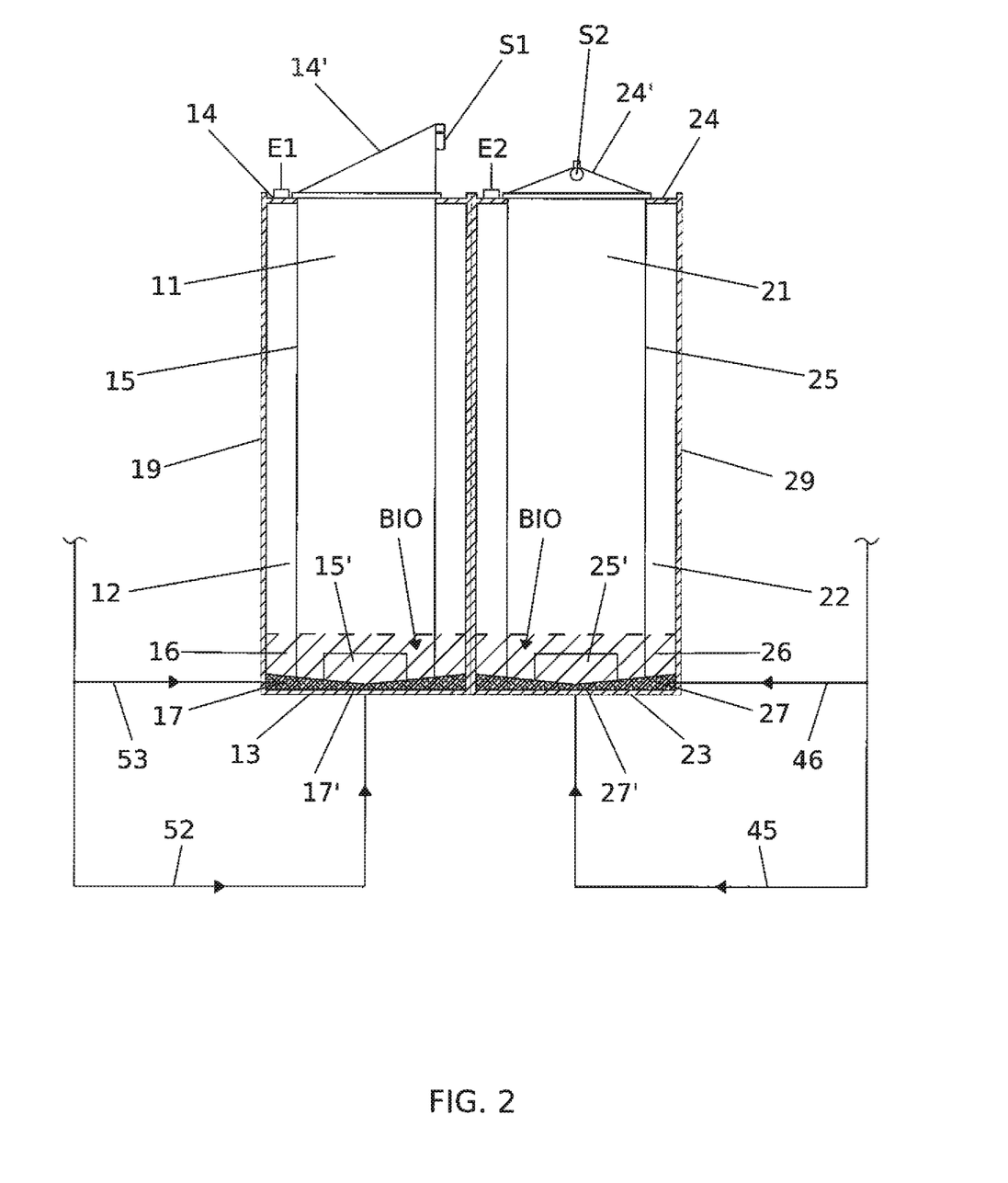
FIG. 2 is a front view, showing on a larger scale two treatment tanks belonging to the facility of FIG. 1.

The waste treatment facility, in accordance with the invention, is shown in its generality in FIG. 1. It first comprises two treatment tanks 1 and 2, which shall be described in more detail in reference to FIG. 2.

The tanks 1 and 2, which are globally identical, have in the example shown a rectangular section. As an alternative, it can be provided that they have other shapes, in particular parallelepipeds with a different section, or cylinders with a circular section or pseudo cylinder with an elliptic section. The dimensions of the tanks are suited according to the nature and the quantity of the flow of substrates to be treated.

Each tank 1 or 2 defines a central cell (or compartment) 11 or 21, also called a tube. The latter is surrounded by an annular peripheral cell (or compartment) 12 or 22, also called a ring. Each tube and each ring are mutually concentric, in the example shown.

Each tank 1 or 2 comprises a bottom 13 or 23, a lid 14, 14' or 24, 24', as well as an outer jacket 19 or 29 connecting this bottom and this lid. This jacket, which forms the peripheral wall of a respective ring, is comprised of four mechanical elements namely, from the outside to the inside:

a vertical outer skin associated with the aforementioned bottom, in order to provide the exoskeleton function;

an insulation layer that can be affixed on the outer or inner faces of this skin;

a preheating circuit which is arranged on the inner faces of this skin and at the cell bottom;

a sealed casing that can be formed either by the inner face of the outer skin itself if its material lends itself to this, or a paint or a sealed coating or by a film or a welded assembly of plastic plates;

an assembly edge by male flange, which extends over the top perimeter of the outer skin in order to cooperate with an assembly edge of a female flange, that extends over the bottom perimeter of the lid;

a compression seal that is inserted between the flange of the outer skin and that of the lid.

Each lid covers the entire volume of the tank, but strictly differentiates the volume of each ring with respect to that of the tube. For this purpose, a separation wall 15 or 25 extends from this lid, in the direction of the bottom. Note that each wall 15 or 25 does not extend over the entire height of the tank, in such a way as to delimit a so-called common zone 16 or 26, in the vicinity of the bottom. In the example shown, each wall 15 or 25 is carved with indentations 15' or 25', in order to provide this communication between a respective ring and tube. It is important to note that the configuration of the indentation zones is easily varied in order to dimension the dynamics of the communications between a ring and a tube.

The two lids 14, 14' or 24, 24' are identical in that each one of them is comprised of two concentric portions, of which the first 14 or 24 covers a respective ring 12 or 22, and of which the second 14' or 24' covers a respective tube 11 or 21. In any case this lid hermetically seals the interior volume of a respective tank. These two lids are on the other hand functionally different, as shown in particular in FIGS. 2 and 3.

Figure 3:
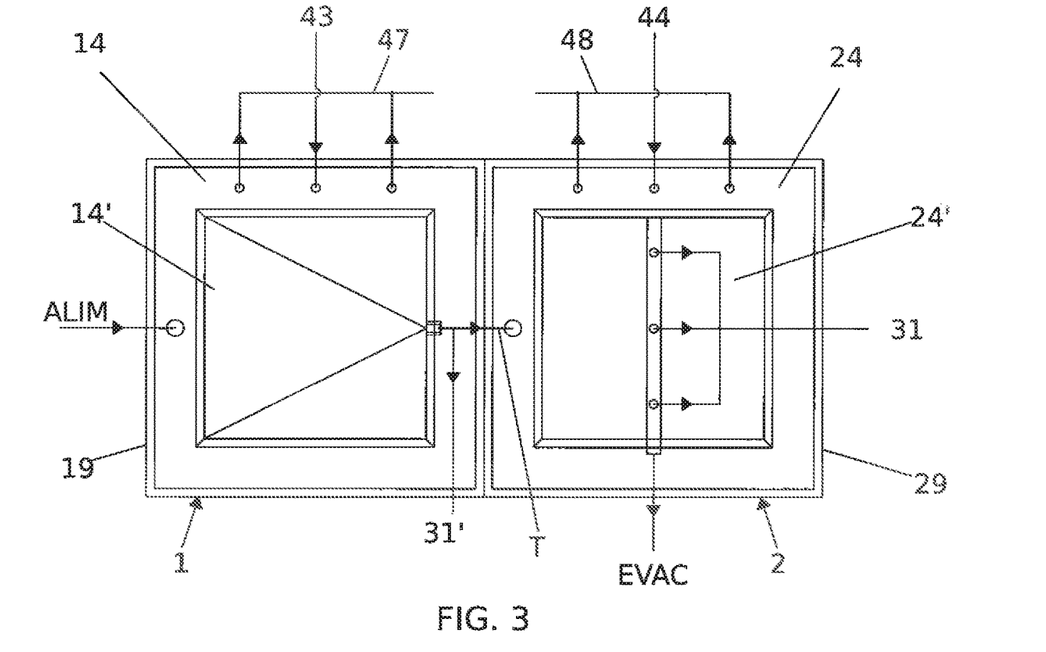
FIG. 3 is a top view, showing these two treatment tanks.
Figure 4:
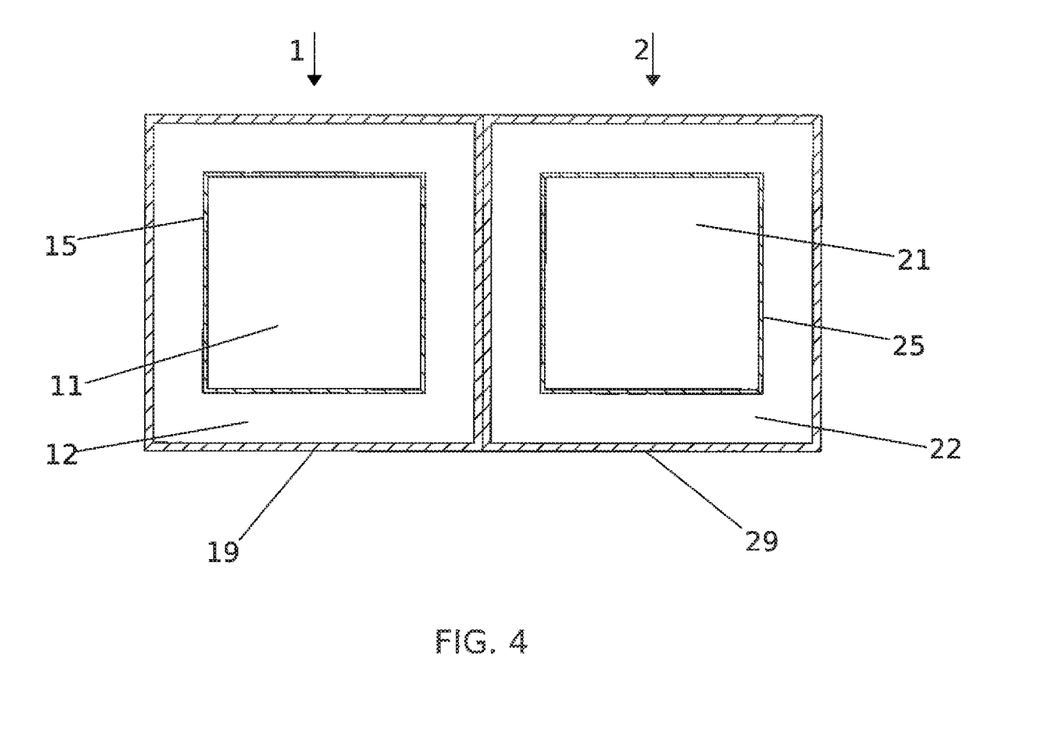
FIG. 4 is a cross-section view of these two tanks.

Indeed, the peripheral portion 14 of the first lid has an inlet E1 (FIG. 2) of raw substrates, via a supply line ALIM (FIG. 3). In addition, the central portion 14' of this first lid has an outlet S1 (FIG. 2) in order to ensure the transfer from the first tube to the second ring, via a transfer line T (FIG. 3). However the peripheral portion 24 of the second lid has an inlet E2 of the partially biodigested substrates, via the aforementioned line T. Note that the outlet S1 is raised with respect to the inlet E2, in order to favour a transfer via gravity of the substrates between the two tanks 1 and 2.

Finally the central portion 24' of this second lid has an outlet S2 (FIG. 2) in order to provide for the discharge of the substrates out of the second tube, via an EVAC line, to the posterior treatment zone of the facility, in particular the wringing of digestates. This outlet S2 is also raised, in order to favour a discharge via gravity of the substrates.

Two ducts 31 and 31' allow moreover for the discharging, out of the tanks, of the biogas and of the micro-bubbling gas which shall be described hereinbelow. Moreover the peripheral portion of each lid is supplied, via lines 43 and 44, with circulation gas able to circulate waste inside the tanks. This peripheral portion also has stirring gas outlets that communicate, via lines 47 and 48, with a filtration or recirculation device of the biogas which will also be described hereinbelow.

Each one of the two tanks 1 or 2 is provided, towards its bottom, with a sealed double bottom, which is slightly concave. This double bottom encloses a stirring device 17 or 27, comprised of a series of nozzles, as well as a micro-bubbling device 17' or 27', comprised of micro-perforated ceramic discs. These nozzles and these discs are of a type known per se in such a way that, in FIG. 2, they are shown diagrammatically.

The facility in accordance with the invention further comprises different mechanical members, of the conventional type, of which some are shown in FIG. 1.

There is first of all a system for wringing substrates at the outlet of the second tube, carried out in the example shown in the form of a wringer screw 3. As an alternative, a centrifuge can be provided, or a simple decantation enclosure. This screw 3 is linked to the second tube via the aforementioned EVAC discharge line, able to convey the substrates exiting from the tank 2. This screw has two outlets, namely an outlet 32 for the digestates and an outlet 33 for the eluates. In the case of an application of the method with inputs with a very low content in solids, in a fixed biomass configuration, it is common that this device for wringing be avoided or replaced with a tangential or through filtration system.

This is furthermore a reservoir, or pressure tank 4, which is connected to the tubes by the ducts 31 and 31' hereinabove, able to convey the biogas exiting from the tank 2. This tank 4 has two outlets, of which one 41 communicates with a filtration device 5, which shall be described in more detail hereinbelow.

Moreover, several recycling lines of the biogas extend from the other outlet 42 of the tank 4. There is:

the aforementioned line 43 which exits in the upper portion of the ring 12, the aforementioned line 44 which exits in the upper portion of the ring 22, a line 45 which exits at the bottom of the tube 21 and supplies the micro-bubbling device 27, as well as a line 46 which supplies the stirring nozzles provided on the outer side wall of the tank 2.

The filtration device 5 of the biogas has for function to separate the $CO_2$ from the methane $CH_4$. It can take the form of a water solubilisation cell, or any other equivalent device. This device 5 is typically supplied with a vacuum via an ATEX class aeraulic pump. It has an outlet line 51 for the filtered methane, as well as two recycling lines:

a line 52 which exits at the bottom of the tube 11 and supplies the micro-bubbling device 17 as well as a line 53 that supplies stirring nozzles not shown, provided on the outer side wall of the tank 1.

The implementation of the facility described hereinabove, shall now be explained in what follows. Note that the facility comprises, in addition to the mechanical members shown in figures, additional members which are not shown. They are of the conventional type and are not part of the invention, in such a way that they are described succinctly in the framework of the aforementioned implementation.

Before being introduced into the treatment tanks, the waste undergoes a crushing of the conventional type, in order to reduce their relative size in a granulometry that does not exceed 25 mm. This crushing can be carried out in a device of the slow crusher type with a double axis blade, supplied by a loading hopper. The latter is typically provided with a lid that provides the protection of the operator and with a hydraulic switch which allows for the lifting and emptying of the wastebins (ISO) of 120 litres or 240 litres.

Downstream of the aforementioned crusher, the waste (also called "substrate") is admitted and contained in a preheating and mixing system, constituted for example of a tank loaded via gravity with this crushed waste. This tank can receive a dilution liquid typically brought to 55° C., comprised of a mixture of eluates, formed downstream of the method, and of water. This tank is typically provided with a tubular network wherein circulates a heating medium providing the definitive heating of the preheated diluted substrate so that the whole reached the target temperature of 55° C.

As a preheating support of the substrates introduced and of the insulation of the tanks, the heating circuit is brought to a temperature higher by a few degrees than that of the target, or 58° C. or 38° C., until the target temperatures measured by sensors in the cells are reached, which causes the stoppage of the circulation of the fluid. Moreover, as soon as the sensors return an indication of a drop in temperature, the heat transfer fluid is then immediately heated and recirculated in order to counter the inertia of the system.

A lifting pump can also be provided, advantageously accepting highly turbid flows with a maximum granulometry of 35 mm. This pump is intended to supply the bioreactor, at the upper portion of the first ring, with the substrate.

Generally, the substrates are admitted by the ALIM line, progress downwards along the first ring under the effect of the biogas admitted by the line 43. In this enclosure they lend themselves to a first step of digestion via anaerobic bio-oxidation, namely a hydrolysis. This first transformation is made possible due to the particularly dense presence of hydrolytic anaerobic bacteria in the first ring. During their passage in this ring, the gas blown from the line 53, thanks to the nozzles 17, generates a turbulent effect from the bottom upwards without however destructuring the granular bacterial biomes that are installed therein and which as such provide a stirring function and prevent the formation of a crust on the surface during the passage of the gas in the non-immersed volume of the ring.

Then the substantially totally hydrolysed substrates progress upwards along the first tube 11, under the combined effect of the biogas admitted by the line 43, and of the gas blown by the line 52. The network of micro-perforated ceramic discs 17, supplied by this line 52, delivers a flow of micro-bubbles with a stirring effect but especially a floating of the sediments. These separate supplies make it possible to separately manage the decompacting and the stirring in the rings and the floating in the tubes outside of or simultaneously with the filling and transfer phases of substrates.

The stirring and floating device operates in a closed circuit in order to prevent on the one hand the discharge of gas and to prevent the risks of overpressure at the top of the tank. Note that this closed circuit even tends to create a vacuum of the tube, in particular in the top portion of the latter, which favours the rising of the substrate inside this tube. During their residence in this tube, the substrates undergo a second step of digestion, namely an acidogenesis, due to the massive presence of acidophilous anaerobic bacteria in this enclosure.

The partially digested bacteria are then transferred, via the line T, to the second tank 2. They progress downwards along the second ring under the effect of the biogas admitted by the line 44. They then undergo a third step of digestion, namely an acetogenesis due to the massive presence of acetotrophic anaerobic bacteria in this enclosure. During their passage in this ring, the gas blown from the line 46, thanks to the aforementioned nozzles, generates a turbulent effect and provides a stirring function identical to what happened in the ring 1.

Then the substrates progress upwards along the second tube 21, under the joint effect of the biogas or of the $CO_2$ admitted on the one hand via the line 44 and, on the other hand, via the line 45. As described hereinabove in the case of the first tank, a stirring effect is produced but especially a floatation effect of the sediments. During their residence in this tube, the substrates undergo the final step of anaerobic digestion, the methanogenesis which is intimately linked to the preceding acetotrophic phase and which is optimised due to the massive presence of methanogenic anaerobic bacteria in this enclosure.

In accordance with the invention, beyond the separation of the phases, a continuous biochemical transition is provided within the bioturbation zone formed at the bottom of each tank, due to the permanence of a volume of the mixture of the substrates at the low point of the rings up to the height of the indentations of the tube that is installed therein. This bioturbation zone is assigned the reference BIO in FIG. 2. Also note the existence of a bioturbation zone with sediment dynamics, namely in other terms gravity, carried out from the top point of the second ring to the bottom zone of the second tank.

The injecting of gas flows at regular but brief intervals at the level of the rings or of the tubes, outside of the filling and transfer phases and during the transfer phases produces a stirring and a non-destructive decompacting of the microbiological biomes inducing a granulation of the settled solids. The injecting of gas flows into the tubes, during the filling and transfer phases and outside of the transfer phases as much as needed, results in the rising via flotation of the sediments and favours the transport thereof upwards in the transfer dynamics.

In general the gas, namely biogas and/or $CO_2$, that is injected/recycled in the tanks, provides three main hydraulic and aeraulic functions: circulation, stirring, micro-bubbling and a biochemical function by supplying either associable hydrogen ($H_2S$) or carbon ($CO_2$). Those skilled in the art will adjust in particular the operating conditions and the unfolding of each one of these three steps, according to the parameters of the substrate and of the bacterial speciation according to the four different phases in the four enclosures of the biodigester. The operating conditions are in particular the choice of injecting raw biogas or more or less purified in $CO_2$ or $H_2S$ or only $CO_2$. Those skilled in the art will also adapt the respective gas flow rates and the diameters of the respective bubbles in order to carry out each function. The unfolding of the steps comprises in particular their duration, their frequency, the possible concomitance between these steps. The parameters of the substrate comprise in particular their nature, their turbidity, their coalescence, as well as their flow rate.

The substrates digested in a substantially complete manner are then discharged, via the line EVAC, to the screw 3. They are then separated, in a manner known per se, into a substantial solid fraction or digestates, extracted via the line 33, and a substantially liquid fraction or eluates, via the line 32.

Moreover, biogas is discharged in the direction of the tank 4, via the line 31. A first portion of this biogas is recycled in the direction of tanks 1 and 2, via the lines 43 to 46. The other portion of this biogas is directed, via the line 41, to the filtration device 5, where it is separated into a fraction rich in methane discharged by the line 51, as well as a fraction rich in $CO_2$ recycled by the lines 52 and 53.

Note that, in the example shown, biogas and $CO_2$ are recycled in the direction of the tanks. As an alternative, only the biogas or only the $CO_2$ can be recycled. As an additional alternative, both the biogas and the $CO_2$ can be recycled, but at places of the tanks that are different from those shown in the figures.

More precisely, it is assumed that we are in the initial phase of the implementation, which corresponds to the very first introduction of substrates into the first tank 1. The fraction of waste introduced as such resides first in the ring of this first tank then, under the effect of the circulation gas, is transferred to the tube of the first tank. Once filled, the tube 1 carries out a transfer to the ring 2 of the tank 2 for a volume equivalent to that of the raw substrates introduced into the ring 1. The filling of the ring 2 and of the tube 2 continues at the rate of the introduction of the raw substrate upstream in the system. As soon as the tube 2 is filled it is now assumed that we are in the "normal" regime of implementation. It can easily be seen that in this normal regime the method in accordance with the invention is of the continuous discretised type, namely it opposes a treatment of the "batch" type, but it is not generally rigorously continuous as it could be in the case of production of substrates coming for example from a method of the agro-industrial type which itself is continuous.

In this "normal" configuration, the work is carried out in two steps:

The second ring receives in the top portion an injection of biogas enriched with biogas or $CO_2$ under pressure. Being sealed it then acts as a pressure chamber wherefrom takes place a transfer of non-compressible fluids namely the rise of the substrates contained in the second tube. The latter, which is open outwards in the direction of the wringer screw, then behaves as an expansion duct.

Once a volume of exiting substrate, which is equivalent to that of the substrate to be introduced into the bioreactor, has been discharged from the second tank according to the step described hereinabove, biogas or $CO_2$ is injected under a suitable pressure into the first ring, so that it transfers the substrate into the first tube. Since the latter is open at its top point to the second ring, the substrate is transferred, at the end of the course of expansion, to the top point of the second ring via the line T.

At the same time as the biogas or $CO_2$ is injected into the second ring, an intensive but brief micro-bubbling is carried out at the foot of the second tube. This generates a driving of the sediments upwards during the transfer of a dose in the expansion system along the tube. A similar micro-bubbling is carried out in the first tank, at the moment when the biogas is injected under pressure at the top point of the ring 1.

A network of sensors not shown measure in real time or slightly differed the values obtained for different parameters, such as: the temperature, the pH, the turbidity of the substrates during the different phases, the chemical composition, the temperature and the relative humidity of the biogas and of the purified biomethane but also the level of the substrates in the different tanks.

A set of several programmable logic controllers not shown process the signals received from the sensors, infer the behaviour of effectors and report on the state of the system on a remote control station.

A network of effectors not shown such as hydraulic or pneumatic solenoid valves regulate the circulation of the flows of substrates, digestates, eluates controlled by the programmable controllers or directly by the human operator.

A hydraulic network not shown transports eluates to be used as a de-coagulation fluid to the critical points of the substrate transfer pipes.

A fraction of the loop of the heating circuit, not shown, passes through a heat exchanger which is sourced by the cooling device of the electric generator and as such transmits calories to the heat transfer fluid circulating in the heating circuit of the facility.

The invention is not limited to the examples described and shown. As such, in the embodiment described hereinabove, the means for circulating the waste, from the first ring to the second tube, are of the pneumatic type. As an alternative not shown, it can be provided that these means for circulating the waste are non-destructive means of pumping. In this case, this is more specifically pumps of the peristaltic or lobe type, which allow for the transfer from the first tube 1 to the second ring without destroying the bacterial biomes. The circulation of the waste pneumatically is preferred, as it is more respectful of the materials transferred and because it does not make use of any mobile mechanical part, which is subject to wear and requiring specific maintenance.

The dimensional characteristic of the different constituents of the facility are determined first by a set of physical-chemical factors that influence the volume of the tanks, on their diameter but especially on their height. These stresses therefore depend on the technical feasibility of the method.

Moreover economic and contextual factors can also influence the sizing through the effect of budgetary, environmental, or cultural constraints.

Considering that the transfers of substrates are the result of a downward thrust exerted by a gas pressurised in a chamber delimited by the interior face of the lid on the ring and the surface of the substrate contained in the ring, that this gas pressure induces an overpressure of the gases dissolved in the substrates, that the hydrogen has a pressure of 2 bars inhibits a significant portion of the biochemical reactions of the sequence of the four phases of the methane digestion, we have determined a limit to the size of the cells over two magnitudes, the height and the volume of the ring, by considering a highly turbid substrate titrating up to 55% of total solids.

Indeed the higher the volume to be transferred is and the more turbid the substrate is, the higher the thrust force has to be to overcome both the mass and the friction that generate load losses.

The high variability of the configurations that can be made makes it practically impossible to model the limit values with a high degree of precision because the width of the ring, its height, the type of substrate and the parameters that determine the friction forces on regular and singular configurations creating load losses have to be taken into account. We therefore had recourse to a summary experimental approach as a prototype for determining the limit values that do not deliver the holistic field of feasibility of the method but only thresholds that we have adopted for the safety that they provide in a certain zone of feasibility.

These dimensional thresholds advantageously translate into the following typical values, provided on a non-limiting basis:

Maximum height of the substrate in the tanks: between 7 metres and 10 metres.

Maximum width of the ring: between 1.5 metres and 2.5 metres.

Maximum diameter of the tube: between 3 metres and 4 metres.

Maximum turbidity of the substrate: between 55% and 75% of total solids in suspension.

Moreover the inventors have considered the need to optimise the thermodynamics of the system which is thermophilic (55° C.) by considering the fact that beyond a volume of about 500 m$^3$ the heat transfers and the aeraulic stirring exceeded the acceptability threshold for energy consumption that we had set to 25% of the production capacity drawn from the recycling of the biomethane.

As a purely non-limiting example, in order to produce a commercial offering adapted to the targets aimed by the inventor, the latter has broken down the facility that has just been described into several models that vary according to their treatment capacity and the type of substrate to be treated. One of these models is configured to be sheltered in two sea containers of the "20' high Cube" type, in terms of the ISO standard from 1967, which are arranged flat. The first container contains the bioreactors, the loading hopper associated with the crusher and with the dilution and pre-heating tank, as well as a supply pump. The second container is reserved for the electrical cabinet, at the control station, the extruder screw, electric generators and filters for the biogas.

This extremely compact and versatile equipment is also modular since it is possible to add up to three "bioreactor containers" in order to increase the treatment capacities of the plant according to its needs at the moment, without the technical container being under-sized. With such a facility an operator can treat every day up to 1 $m^3$ of crushed and diluted substrate, which represents for example about 375 kg of kitchen and service waste and 25 kg of grease coming from a grease tank. In this configuration the production of biomethane will be about 34.5 $Nm^3$ per day, the liquid digestates or eluates are produced at about 0.14 $m^3$ per day and the solid digestates after extrusion at about 0.35 $m^3$ per day.

The invention claimed is:

1. A facility for treating organic waste to produce biogas and recover at least one portion of the biogas produced, the facility comprising:
   a first tank including:
      a first separation device extending over a portion of the height of the first tank to define a first central compartment, a first peripheral compartment, closed at an upper portion thereof, and a first stirring and biochemical exchange compartment having a first stirring device arranged at a bottom portion of the first tank, and which is to facilitate stirring and biochemical exchanges, and exclusively provide a fluidic communication between the first central compartment and the first peripheral compartment,
   a second tank including:
      a second separation device extending over a portion of the height of the second tank to define a second central compartment, a second peripheral compartment, closed at an upper portion thereof, and a second stirring and biochemical exchange compartment having a second stirring device arranged at a bottom portion of the second tank, and which is to facilitate stirring and biochemical exchanges, and exclusively provide a fluidic communication between the second central compartment and the second peripheral compartment,
   a supply line to feed the organic waste into the first peripheral compartment;
   a transfer line to transfer partially treated organic waste from the first central compartment to the second peripheral compartment in a manner that the first central compartment communicates at the upper portion thereof via a pipe exclusively with a top of the second central compartment;
   a discharge line to discharge the treated organic waste from the second central compartment; and
   a pressure tank and at least one circulating gas line, in fluidic communication with the pressure tank, to circulate the organic waste by pneumatic force from the first peripheral compartment to the second central compartment; the at least one circulating gas line including:
      a first circulation gas line and a second opening into the upper portion of the first peripheral compartment to facilitate creation of a pressure in a gas blanket of the first peripheral compartment which causes to rise of a volume of organic substrate in the first central compartment by pneumatic force that corresponds to a volume of incoming organic waste, and, and
      a second circulation gas line opening into the upper portion of the second peripheral compartment to facilitate discharge by pneumatic force of a volume of digestates corresponding to a volume of incoming organic waste from the second central compartment;
   wherein the facility is arranged in a manner that the organic waste to be treated is transferred in succession from a first volume formed by the first peripheral compartment, then to a second volume formed by the first central compartment, then to a third volume formed by the second peripheral compartment, then to a fourth volume formed by the second peripheral compartment, before being discharged by pneumatic force from the second peripheral compartment by a pipe from the second tank via a semi-continuous feed.

2. The facility of claim 1, wherein the pressure tank and at least one circulating gas line are to pneumatically circulate the organic waste.

3. The facility of claim 2, wherein the pressure tank is to pressurize a biogas, nitrogen, or carbon dioxide, and the at least one circulating gas line is to convey biogas, nitrogen, or carbon dioxide from the pressure tank to the first peripheral compartment and/or the second peripheral compartment.

4. The facility of claim 2, wherein the pressure tank and the at least one circulating gas line are in fluidic communication with the first peripheral compartment and the second peripheral compartment.

5. The facility of claim 1, wherein the pressure tank and at least one circulating gas line are to non-destructively circulate the organic waste.

6. The facility of claim 1, wherein the transfer line is to define a zone for biochemical exchange and transition.

7. The facility of claim 1, wherein:
   the first stirring device comprises a series of nozzles, provided on a sidewall of the first peripheral compartment, and to which is supplied a biogas, nitrogen or carbon dioxide; and
   the second stirring device comprises a series of nozzles, provided on a sidewall of the second peripheral compartment, and to which is a biogas, nitrogen or carbon dioxide.

8. The facility of claim 1, wherein the transfer line is to fluidically connect an outlet of the first tank and an inlet of the second tank, said outlet being at a height that is greater than a height of said inlet.

9. The facility of claim 1, further comprising:
   a first sediment floating system including at least one first sediment duct to convey a biogas, nitrogen, or carbon dioxide, to supply at least one first micro-bubbling device provided adjacent a bottom of the first central compartment; and
   a second sediment floating system including at least one first sediment duct to convey a biogas, nitrogen, or carbon dioxide, to supply at least one second micro-bubbling device provided adjacent a bottom of the second central compartment.

10. The facility of claim 1, wherein:
the first central compartment and the first peripheral compartment are in fluidic communication only at a bottom of the first tank, via the first stirring and biochemical exchange compartment; and
the second central compartment and the second peripheral compartment are in fluidic communication only at a bottom of the second tank, via the second stirring and biochemical exchange compartment.

11. A method for implementing an organic waste treatment facility, the method comprising:
providing a first tank that includes a first separation device extending over a portion of the height of the first tank to define a first central compartment, a first peripheral compartment, a first stirring and biochemical exchange compartment having a first stirring device arranged at a bottom portion of the first tank, and which is to facilitate stirring and biochemical exchanges, and provide a fluidic communication between the first central compartment and the first peripheral compartment, and a second tank that includes a second separation device extending over a portion of the height of the second tank to define a second central compartment, a second peripheral compartment, and a second stirring and biochemical exchange compartment having a second stirring device arranged at a bottom portion of the second tank, and which is to facilitate stirring and biochemical exchanges, and provide a fluidic communication between the second central compartment and the second peripheral compartment;
admitting organic waste to be treated into the first tank;
conducting, at least partially, a hydrolysis process in the first peripheral compartment and, at least partially, an acidogenesis process in the first central compartment;
transferring the partially treated organic waste from the first central compartment to a second peripheral compartment;
conducting, at least partially, an acetogenesis process in the second peripheral compartment and, at least partially, a methanogenesis process in the second central compartment; and
discharging the treated organic waste from the second central compartment.

12. The method of claim 11, further comprising the organic waste from the first peripheral compartment to the second central compartment.

13. The method of claim 11, further comprising:
extracting a gaseous fraction rich in biogas from the treated organic waste; and
transferring at least one portion of the extracted gaseous fraction back into at least one of the first tank or the second tank.

14. The method of claim 11, further comprising:
extracting a gaseous fraction rich in carbon dioxide from the treated organic waste; and
transferring at least one portion of the extracted gaseous fraction back into at least one of the first tank or the second tank.

15. The method of claim 11, further comprising:
discharging a fraction of the organic waste present in the second tank; and
admitting another fraction of the organic waste into the first tank, with the discharged fraction and the admitted fraction having substantially the same volumes.

16. The method of claim 11, further comprising:
assigning different biological retention times to the first central compartment and the first peripheral compartment; and
assigning different biological retention times to the second central compartment and the second peripheral compartment.

17. A facility for treating organic waste to produce biogas and recover at least one portion of the biogas produced, the facility comprising:
a first tank including:
a first separation device defining a first central compartment, a first peripheral compartment that is closed at an upper portion thereof, and a first stirring and biochemical exchange compartment having a first stirring device which is to facilitate stirring and biochemical exchanges in the first tank, the first stirring and biochemical exchange compartment to exclusively provide a fluidic communication between the first central compartment and the first peripheral compartment at a bottom portion of the first tank,
a second tank including:
a second separation device defining a second central compartment, a second peripheral compartment that is closed at an upper portion thereof, and a second stirring and biochemical exchange compartment having a second stirring device which is to facilitate stirring and biochemical exchanges in the second tank, the second stirring and biochemical exchange compartment to exclusively provide a fluidic communication between the second central compartment and the second peripheral compartment, and
a supply line to feed the organic waste into the first peripheral compartment;
a transfer line to transfer partially treated organic waste from the first central compartment to the second peripheral compartment in a manner that the first central compartment communicates at the upper portion thereof exclusively with a top of the second central compartment;
a discharge line to discharge the treated organic waste from the second central compartment; and
a pressure tank and at least one circulating gas line, in fluidic communication with the pressure tank, to circulate the organic waste by pneumatic force from the first peripheral compartment to the second central compartment; the at least one circulating gas line including:
a first circulation gas line and a second opening into the upper portion of the first peripheral compartment to facilitate creation of a pressure in a gas blanket of the first peripheral compartment which causes to rise of a volume of organic substrate in the first central compartment by pneumatic force that corresponds to a volume of incoming organic waste, and
a second circulation gas line opening into the upper portion of the second peripheral compartment to facilitate discharge by pneumatic force of a volume of digestates corresponding to a volume of incoming organic waste from the second central compartment;
wherein the organic waste to be treated is transferred in succession from a first volume formed by the first peripheral compartment, then to a second volume formed by the first central compartment, then to a third volume formed by the second peripheral compartment, then to a fourth volume formed by the second peripheral compartment, before being discharged by pneumatic force from the second tank.

\* \* \* \* \*